US00PP36075P2

(12) United States Plant Patent
Miller

(10) Patent No.: US PP36,075 P2
(45) Date of Patent: Aug. 20, 2024

(54) ***CISTUS* PLANT NAMED 'MBNcistus2023'**

(50) Latin Name: *Cistus purpureus*
Varietal Denomination: MBNcistus2023

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 18/532,668

(22) Filed: Dec. 7, 2023

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct *Cistus purpureus* cultivar named 'MBNcistus2023' is disclosed, characterized by very pale pink, nearly white flowers with a dark eye. The new cultivar is a *Cistus*, typically suited for ornamental garden use, or as a cut flower.

1 Drawing Sheet

Latin name of the genus and purpureus: *Cistus purpureus*.
Variety denomination: 'MBNcistus2023'.

BACKGROUND OF THE INVENTION

The new variety originated as a chance discover by the inventor, Luen Miller. The variety was discovered as a naturally occurring branch mutation on a single plant of an unpatented, unnamed variety of *Cistus purpureus*. The new variety was discovered during April of 2020 at a commercial nursery in Royal Oaks, California in a commercial planting of the parent variety.

After selecting and isolating the new cultivar, asexual reproduction of the new cultivar 'MBNcistus2023' was first performed at a commercial nursery in Royal Oaks, California in April of 2020. Vegetative terminal cuttings were used for propagation. The inventor continued confidential, controlled evaluation and propagation of 'MBNcistus2023', to establish a stable clone. 'MBNcistus2023' has since produced two generations and has shown that the unique features of this cultivar are stable and reproduced true to type. Typical asexual reproduction of the new variety is by softwood vegetative cuttings.

SUMMARY OF THE INVENTION

The cultivar 'MBNcistus2023' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MBNcistus2023.' These characteristics in combination distinguish 'MBNcistus2023' as a new and distinct *Cistus* cultivar:

1. Very pale pink, nearly white flowers with a dark eye.

PARENTAL COMPARISON

Plants of the new cultivar 'MBNcistus2023' are similar to the parent in most horticultural characteristics. However, 'MBNcistus2023' differs in the following:

1. The new variety has very pale pink, nearly white flowers with a dark eye; the parent variety has medium pink flowers with a dark eye.

COMMERCIAL COMPARISON

Plants of the new cultivar 'MBNCISTUS2023' can be compared to the commercial unpatented, unnamed variety of *Cistus ladanifer* frequently found in the nursery trade. Plants of 'MBNcistus2023' are similar to plants of *Cistus ladanifer* in most horticultural characteristics, however, plants of 'MBNcistus2023' differ in the following:

1. The new variety has very pale pink, nearly white flowers with a dark eye; this comparator has white flowers with a dark eye.
2. Plants of the new variety are more mounding than the upright plants of *Cistus ladanifer.*
3. Foliage of the new variety is matte and scabrous; foliage of this comparator is glossy and glabrous.

BRIEF DESCRIPTION OF THE PHOTOGRAPH

The accompanying photograph illustrates a comparison of the flower of the new variety (right side of the photo) with a flower of the parent variety (left side of the photos. Plants producing these flowers were approximately 18 months of age, grown in Royal Oaks, CA. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007, except where general terms of ordinary dictionary significance are used. The following observations and measurements describe 'MBNcistus2023' plants grown at a commercial nursery in Royal Oaks, California, under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Cistus purpureus* 'MBNcistus2023'.

Age of the plant described: Approximately 18 months.

Container size of the plant described: 5-gallon commercial container.

ROOTS

Root description: Semi-woody, moderately dense. Colors include Grey-Brown 199A, 199B and 199C.

PLANT

Growth habit: Mounding.

Height: Approximately 40 cm.

Plant spread: Approximately 50 cm.

Branching characteristics: 3 to 4 primary branches at base of plant. These primary branches produce opposite occurring lateral branches at internode intervals of 2.5 cm to 5 cm.

Length of primary branches: Approximately 18 cm to 28 cm.

Diameter of primary branches: Approximately 5 mm.

Length of lateral branches: Approximately 10 cm to 16 cm.

Diameter of lateral branches: Approximately 4 mm.

Branches:

*Texture*.—Mature glabrous with lenticels. Immature rough, nearly hirsute.

*Color*.—Mature: Near RHS Greyed-Purple 183C flushed Greyed-Red 181B. Immature: Near RHs Yellow-Green 144B flushed Greyed-Red 180A.

*Lenticels*.—Density: Not present on youngest growth. Density increases towards base of plant, with oldest wood moderately dense with lenticels. Color: Near RHS White N155C. Height: Average range 1 mm to 2 mm. Diameter: 0.5 mm to 1 mm.

Internode length: Average 3.0 cm.

FOLIAGE

Leaf:

*Arrangement*.—Opposite.

*Quantity*.—Approximately 10 mature and 30 immature per lateral branch.

*Attachment*.—Sessile.

*Leaf internode*.—Average 5 mm.

*Average length*.—3.8 cm to 5 cm.

*Average width*.—8 to 12 mm.

*Shape of blade*.—Elliptic.

*Apex*.—Acute.

*Base*.—Tapered.

*Margin*.—Entire.

*Texture of top surface*.—Non-pubescent, scabrous.

*Texture of bottom surface*.—Non-pubescent, scabrous.

*Appearance of top surface*.—Matte.

*Appearance of bottom surface*.—Matte.

*Color*.—Young foliage upper side: Near RHS Yellow-Green 144A. Young foliage under side: Near RHS Green 138B. Mature foliage upper side: Near RHS Green 137C. Mature foliage under side: Near RHS Green 138B.

*Venation*.—Type: Pinnate. Venation color upper side: Near Green 137C. Venation color under side: Near Green 138B.

FLOWER

Natural flowering season: Flowering from late Spring until late Summer.

Inflorescence type: 3 rotate flowers occur terminally. Sub-terminal nodes produce single, opposite occurring flowers.

Flower longevity on plant: About 8 to 12 days.

Quantity of flowers: 5 flowers per lateral branch. 3 at terminus, 2 at sub-terminus.

Flower size:

*Diameter*.—Approximately 6 cm.

*Depth*.—Approximately 2.2 cm.

Peduncle:

*Length*.—1.5 cm to 2.5 cm.

*Diameter*.—3 mm.

*Color*.—Near Yellow-Green N144D heavily flushed Greyed-Red 181C.

*Texture*.—Hirsute.

Petals:

*Petal arrangement*.—Rotate.

*Length*.—3.5 cm.

*Width*.—4.0 cm.

*Shape*.—Broad deltate.

*Margin*.—Minutely notched along broad apex. Sides entire. Moderately undulate.

*Apex*.—Broad rounded.

*Base*.—Broad cuneate.

*Petal quantity*.—5.

*Texture*.—Soft, glabrous all surfaces.

*Appearance*.—Matte all surfaces.

*Color*.—When opening: Upper surface: Near RHS Red-Purple 69A flushed Purple 75C. Blotch near Red-Purple 59A, minimal feathering. Base Yellow-Orange 17C. Lower surface: Near RHS Purple 75D. Blotch moderately visible as if transparent from upper surface, faint Red-Purple 59A. Base Yellow 9A. Fully opened: Upper surface: Near RHS Red-Purple 69B and 69C. Blotch near Red-Purple 59A, minimal feathering. Base Yellow-Orange 17C. Lower surface: Near RHS Red-Purple 69C and 69D. Blotch faintly visible as if transparent from upper surface, faint Red-Purple 59C. Base Yellow 9C.

Bud:

*Shape*.—Conical.

*Length*.—Approximately 2.0 cm.

*Diameter*.—Approximately 1.5 cm.

*Color*.—Near RHS Green 137C flushed Red-Purple 59A.

Sepals: 3 inner sepals, 2 outer/lower sepals.

*Inner sepals*.—Length: 1.8 cm. Width: 2.0 cm. Shape: Irregular orbicular. Aspect: Strongly reflexed. Color: Interior Surface: Near Yellow-Green 144B. Exterior Surface: Yellow-Green 144A. Texture: Exterior surface rough, nearly hirsute. Interior surface smooth.

*Outer/lower sepals*.—Length: 5 mm to 15 mm. Width: 5 mm. Shape: Rhomboid. Aspect: Rolled under. Color: Upper Surface: Near Yellow-Green 144A. Lower Surface: Yellow-Green 144B. Texture: Smooth all surfaces.

Fragrance: Faint, musty.

REPRODUCTIVE ORGANS

Stamens:

*Quantity*.—Average 100 to 120.

*Filament length*.—Average 7 mm.

*Filament color*.—Yellow 7C.

Anthers:

*Length*.—1.5 mm.

*Shape*.—Oblong.

*Color*.—RHS Yellow-Orange 24A.

Pistil:

*Number*.—3, tightly fused to appear as 1.

*Length*.—8 mm.

*Style*.—1, fused at top of ovary. Length: Approximately 2 mm. Color: Near RHS Yellow-Orange 18C.

Stigma: Single flattened disc at top of style.

*Color*.—RHS Yellow-Orange 18C.

OTHER CHARACTERISTICS

Seeds and fruits: Fruit: Capsule, about 8 mm in diameter and length. Colored near Grey-Brown 199A. Seeds about 1 mm wide and 3 mm long, colored near Greyed-Orange 175C. Viability unknown.

Disease/pest resistance: Neither resistance nor susceptibility to pathogens and pests common to *Cistus purpureus* have been observed.

Temperature tolerance: The new variety tolerates temperatures within USDA zones 7 to 10.

What is claimed is:

1. A new and distinct cultivar of *Cistus* plant named 'MBNcistus2023' as herein illustrated and described.

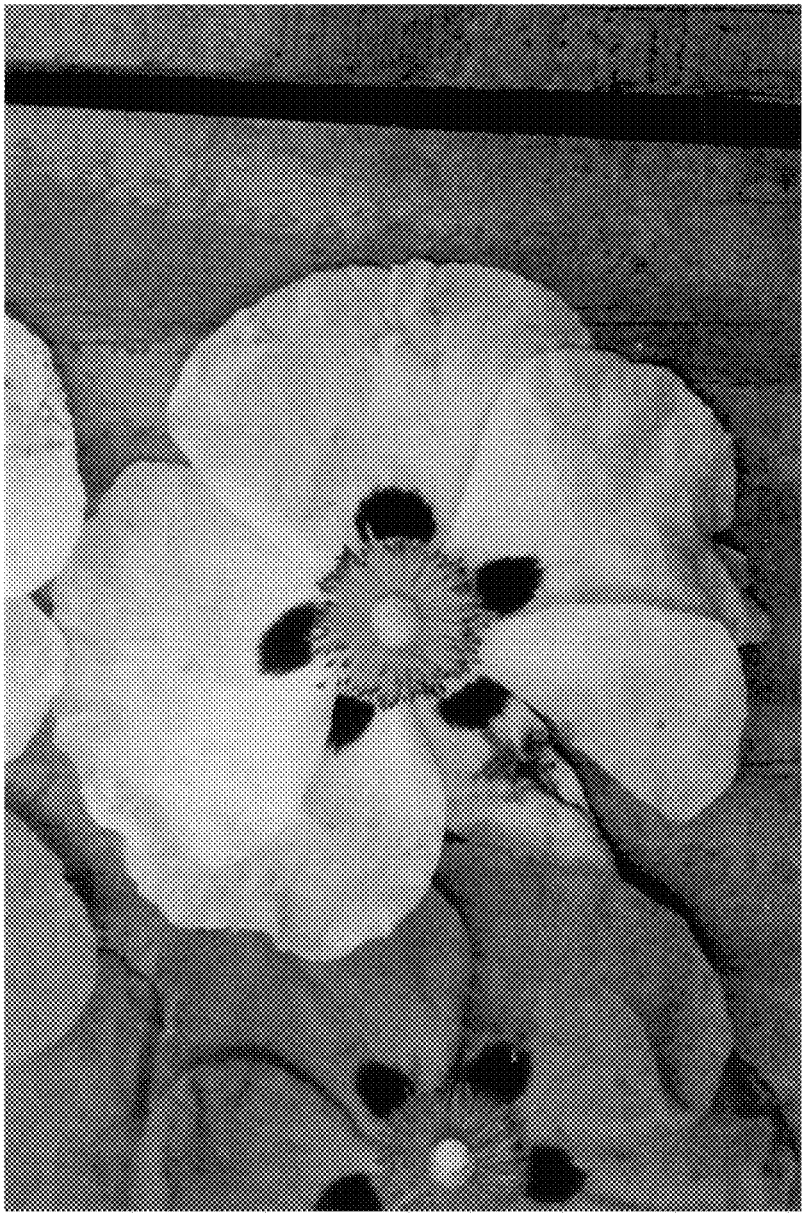

* * * * *